US00PP26127P3

(12) United States Plant Patent
Nir

(10) Patent No.: US PP26,127 P3
(45) Date of Patent: Nov. 24, 2015

(54) ***CAPSICUM ANNUUM* PLANT NAMED 'SLP2B322'**

(50) Latin Name: *Capsicum annuum*
Varietal Denomination: SLP2B322

(71) Applicant: Syngenta Participations AG, Basel (CH)

(72) Inventor: Binyamin Nir, Shikmim (IL)

(73) Assignee: Syngenta Participations AG, Basel (CH)

( * ) Notice: Subject to any disclaimer, the term of this patent is extended or adjusted under 35 U.S.C. 154(b) by 36 days.

(21) Appl. No.: 13/987,940

(22) Filed: Sep. 17, 2013

(65) Prior Publication Data

US 2014/0165245 P1 Jun. 12, 2014

(30) Foreign Application Priority Data

Dec. 6, 2012 (NL) ..... PPS1433 PVP

(51) Int. Cl.
*A01H 5/00* (2006.01)
*A01H 5/08* (2006.01)

(52) U.S. Cl.
USPC ..... Plt./258
CPC ..... *A01H 5/08* (2013.01)

(58) Field of Classification Search
USPC ..... Plt./258
See application file for complete search history.

(56) References Cited

U.S. PATENT DOCUMENTS

2010/0333228 A1 12/2010 Shirai
2013/0298292 A1 11/2013 Bar et al.

FOREIGN PATENT DOCUMENTS

WO 20130078319 5/2013

*Primary Examiner* — Keith O. Robinson
(74) *Attorney, Agent, or Firm* — Karen A. Magri

(57) ABSTRACT

A new *Capsicum annuum* plant named 'SLP2B322' distinguished by its combination of seedless fruits, a glossy and medium-dark red mature fruit colour, fruit diameter of about 3 to 3.5 cm, fruit weight of about 20 to 30 grams, and ability to set fruit under relatively hot conditions.

2 Drawing Sheets

Latin name of the genus and species of the plant claimed: *Capsicum annuum.*
Varietal denomination: 'SLP2B322'.

CROSS-REFERENCE TO RELATED APPLICATIONS

This application claims the benefit under 35 U.S.C. §119(f) from Netherlands Plant Variety Rights application No. PPS1433, filed Dec. 6, 2012.

BACKGROUND OF THE NEW PLANT

The present invention comprises a new and distinct cultivar of *Capsicum annuum,* designated 'SLP2B322'.

The new *C. annuum* 'SLP2B322' was discovered and selected as a single plant in Gedera, Israel in 2010, from the progeny of a cross between SC09-F4-33-b as the female parent (not patented) and AJ06-F3-378-19 as the male parent (not patented).

The new cultivar was first asexually propagated by root cuttings in Bet Dagan, Israel in February, 2010 and has been asexually propagated since that time by cutting and rooting in Gedera, Israel and Almeria, Spain. The distinctive characteristics of this new *C. annuum* are stable and reproduce true to type through successive generations of asexual reproduction.

SUMMARY OF THE INVENTION

"SLP2B322" is a distinctive variety of *C. annuum* characterized by the following traits, which have been repeatedly observed and in combination distinguish 'SLP2B322' as a new and distinct *C. annuum* cultivar:

1. Seedless fruits
2. Glossy, medium-dark red mature fruit colour
3. Fruit diameter of about 3 to 3.5 cm
4. Fruit weight of about 20 to 30 grams.
5. Ability to set fruit under relatively hot conditions (e.g., 30° C. to 35° C. during the day and 25° C. to 30° C. at night).

Essentially all of the fruits of cultivar 'SLP2B322' are completely seedless. However, in cases where 'SLP2B322' has been grown in the vicinity of a fertile variety, there are occasional fruits with seeds due to cross-pollination by insects transferring pollen from the fertile variety to 'SLP2B322'.

BRIEF DESCRIPTION OF THE DRAWINGS

The accompanying photographs show typical characteristics of the new cultivar.

FIG. 1 shows plants of cultivar 'SLP2B322' growing in a plastic greenhouse in Mivtahime, Israel. This image was taken in December 2012, five and one-half months after planting.

FIG. 2 shows mature fruits of cultivar 'SLP2B322'.

DETAILED BOTANICAL DESCRIPTION OF THE NEW CULTIVAR

The following is a detailed botanical description of a new and distinct variety of *C. annuum* known as 'SLP2B322'. Those skilled in the art will appreciate that certain characteristics will vary with older or younger plants. Further, 'SLP2B322' has not been observed under all possible environmental conditions. Where dimensions, sizes, colours and other characteristics are given, it is to be understood that such characteristics are approximations or averages set forth as accurately as practicable. The variety may differ from the descriptions set forth herein with variations in environmental and cultural conditions. Colour determinations are in accordance with the 2001 Edition of The Royal Horticultural Society Colour Chart. 'SLP2B322' is able to set fruit throughout the year when grown in a plastic greenhouse in southern Israel, including under cold (November to March) and hot (April to June) temperatures, although the set is reduced in July and August under these conditions.

A technical description of the variety is provided below in Table 1 based upon observations of 5-month-old plants grown under greenhouse conditions in Gedera, Israel during the Fall season.

TABLE 1

| Characteristic | Value |
|---|---|
| Short technical description | Bush-type plant, indeterminate growth habit, medium internodes, produces seedless fruit, good ability to set in relatively hot conditions |
| Method of reproduction | vegetatively propagated |
| Plant: length of stem (between the ground and first fruit) (cm) | short-medium: 30 |
| Plant: shortened internodes (in upper part) | absent (indeterminate) |
| Plant: number of internodes between 1st flower and shortened internodes (Varieties with shortened internodes only) | none |
| Plant: length of internodes (on primary side shoots)(varieties without shortened internodes) (cm) | medium: 5 to 15 |
| Plant: anthocyanin coloration of nodes | present |
| Stem: Intensity of anthocyanin coloration of nodes | medium-strong |
| Stem: hairiness of nodes | weak |
| Plant: vigor | strong |
| Plant: height (cm) | compact: 200 |
| Leaf: length of blade (cm) | medium: 17 |
| Leaf: intensity of green colour | medium |
| Leaf: shape | ovate |
| Leaf: blistering | weak |
| Leaf: profile in cross section | moderately concave |
| Leaf: glossiness of upper leaf | very weak - weak |
| Leaf: Undulation of margin | medium |
| Leaf: width of blade (cm) | medium: 9 |
| Flower: anthocyanin coloration in anther | absent |
| Peduncle: attitude | semi-drooping |
| Time of beginning of flowering (1st flower on 2nd flowering node) | medium |
| Fruit: colour (before maturity) | green |
| Fruit: intensity of colour (before maturity) | medium |
| Fruit: anthocyanin coloration (before maturity) | absent |
| Fruit: general impression | conical |
| Fruit: attitude | horizontal |
| Fruit: length (cm) | short - medium: 6 to 9 |
| Fruit: diameter (cm) | small: 3 to 3.5 |
| Fruit: ratio length-diameter | medium: 2.35 |

TABLE 1-continued

| Characteristic | Value |
|---|---|
| Fruit: shape in longitudinal section | triangular |
| Fruit: shape in cross section (at level of placenta) | circular |
| Fruit: sinuation of pericarp at basal part | very weak |
| Fruit: sinuation of pericarp excluding basal part | absent or very weak |
| Fruit: texture of surface | smooth or very slightly wrinkled |
| Fruit: colour (at maturity) | red (RHS 32A, 42A & 43A) |
| Fruit: intensity of colour (at maturity) | medium-dark |
| Fruit: glossiness | strong |
| Fruit: stalk cavity | absent |
| Fruit: depth of stalk cavity | very shallow |
| Fruit: shape of apex (PBR) | very acute |
| Fruit: depth of interloculary grooves | very shallow |
| Fruit: number of locules | predominantly two |
| Fruit: thickness of flesh (mm) | thin: 2 to 3 |
| Stalk: length (cm) | medium: 3.5 to 4.5 |
| Fruit: capsaicin in placenta | absent |
| Stalk: thickness (mm) | medium: 3 |
| Calyx: aspect | non enveloping |
| Seed | Absent |
| Time of maturity (from flowering to mature fruit) (days) | medium: 60 (summer); 90 (winter) |
| Ripening can be compared with: | KAPPY |
| Potato Virus Y pathotype 0 | S |
| Potato Virus Y pathotype 1 | Unknown |
| Potato Virus Y pathotype 2 | Unknown |
| Tobamovirus pathotype P0 | S |
| Tobamovirus pathotype P0, P1 | S |
| Tobamovirus pathotype P0, P1, P1-2 | S |
| Tobamovirus pathotype P0, P1, P1-2, P1-2-3 | S |
| Tomato Spotted Wilt Virus | S |

These and other features and characteristics of cultivar 'SLP2B322' are apparent from FIGS. 1 and 2.

Comparisons with Other *C. annuum* Cultivars

'SLP2B322' is most similar to commercial *C. annuum* cultivar 'SLP2B131', which is also a seedless variety. As shown in Table 2, 'SLP2B322' can be distinguished from cultivar 'SLP2B131' (not patented) at least with respect to fruit diameter, fruit weight, mature fruit colour, and season for fruit setting.

TABLE 2

| SLP2B322 has in comparison with: | | | |
|---|---|---|---|
| DENOMINATION OF COMPARISON VARIETY | CHARACTERISTIC IN WHICH THE COMPARISON VARIETY IS DIFFERENT FROM SLP2B322 | STATE OF EXPRESSION OF COMPARISON VARIETY | STATE OF EXPRESSION OF SLB2B322 |
| SLP2B131 | Fruit diameter | 2-3 cm | 3-3.5 cm |
| SLP2B131 | Fruit weight | 20 to 30 g | 10 to 20 g |
| SLP2B131 | Mature fruit colour | Dark red (RHS 46A to 46B) | Medium-dark red (RHS 32A, 42A & 43A*) |
| SLP2B131 | Fruit setting season | Late (moderate temperatures needed for good set) | Early (Can set even in high temperatures) |

*The mature fruits of 'SLB2B322' are very glossy, whereas the color chips in the RHS colour chart are matte, making it more difficult to assign colour chart designations that correspond to the mature fruit colours. The colour of the mature fruits is described as accurately as reasonably possible given this limitation.

A comparison with the antecedent plants, SC09-F4-33-b and AJ06-F3-378-19, is shown below in Table 3. 'SLP2B322' can be distinguished from SC09-F4-33-b at least with respect to fruit size and mature fruit colour, and from AJ06-F3-378-19 at least with respect to mature fruit colour.

TABLE 3

| SLP2B322 has in comparison with: | | | |
|---|---|---|---|
| CHARACTERISTIC IN WHICH THE COMPARISON VARIETY IS DIFFERENT FROM SLP2B322 | STATE OF EXPRESSION OF SLB2B322 | STATE OF EXPRESSION OF SC09-F4-33-b | STATE OF EXPRESSION OF AJ06-F3-378-19 |
| Fruit length (cm) | 6 to 9 | 4 | 8 |
| Fruit diameter (cm) | 3 to 3.5 | 3.5 | 3.5 |

TABLE 3-continued

| SLP2B322 has in comparison with: | | | |
|---|---|---|---|
| CHARACTERISTIC IN WHICH THE COMPARISON VARIETY IS DIFFERENT FROM SLP2B322 | STATE OF EXPRESSION OF SLB2B322 | STATE OF EXPRESSION OF SC09-F4-33-b | STATE OF EXPRESSION OF AJ06-F3-378-19 |
| Mature fruit colour | Medium-dark red (RHS 32A, 42A & 43A) | Dark red (RHS 46A to 46B) | Orange (RHS N30A & 28A) |

What is claimed is:

1. A new and distinct variety of *Capsicum annuum* plant named 'SLP2B322', substantially as described and illustrated herein.

* * * * *

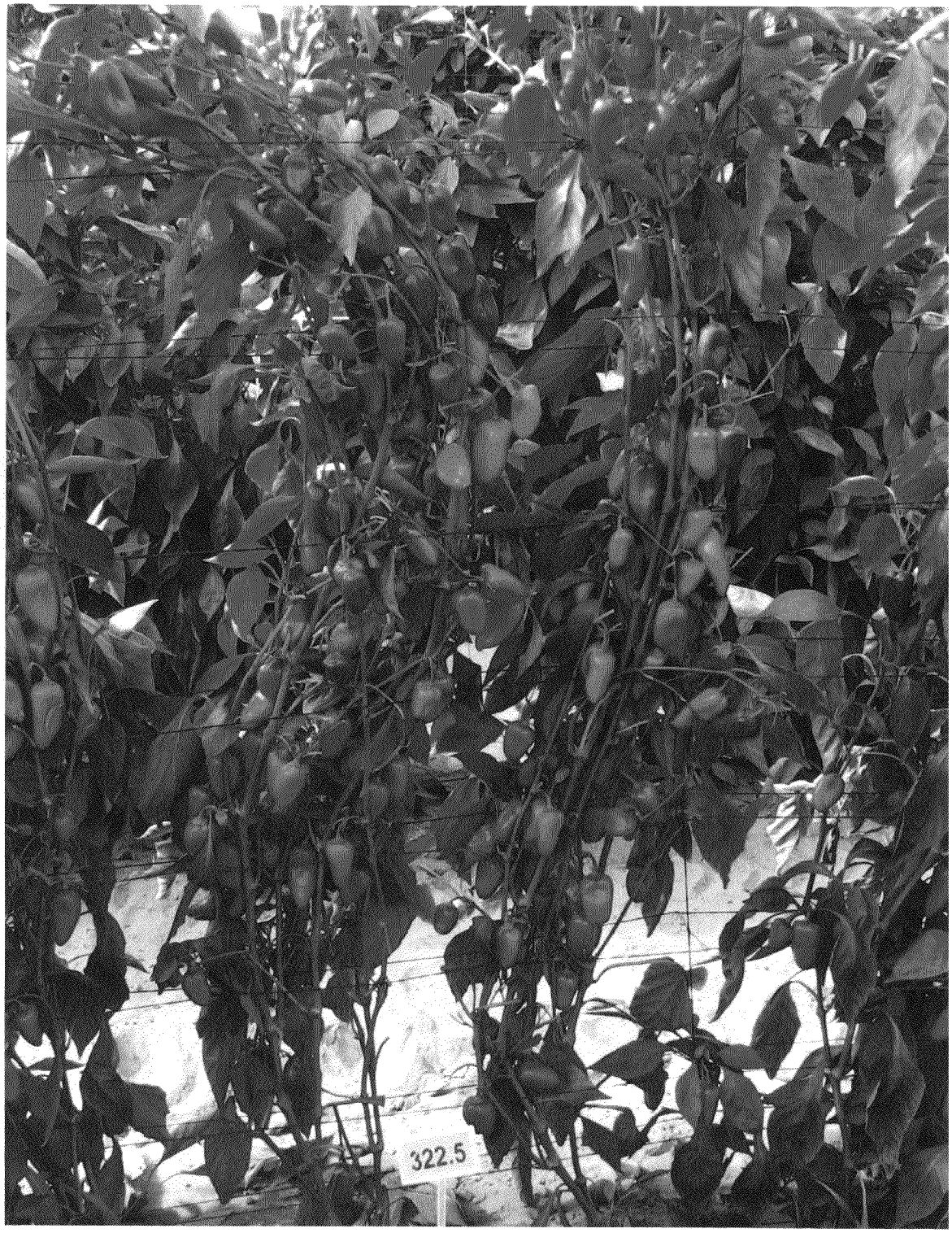
322.5

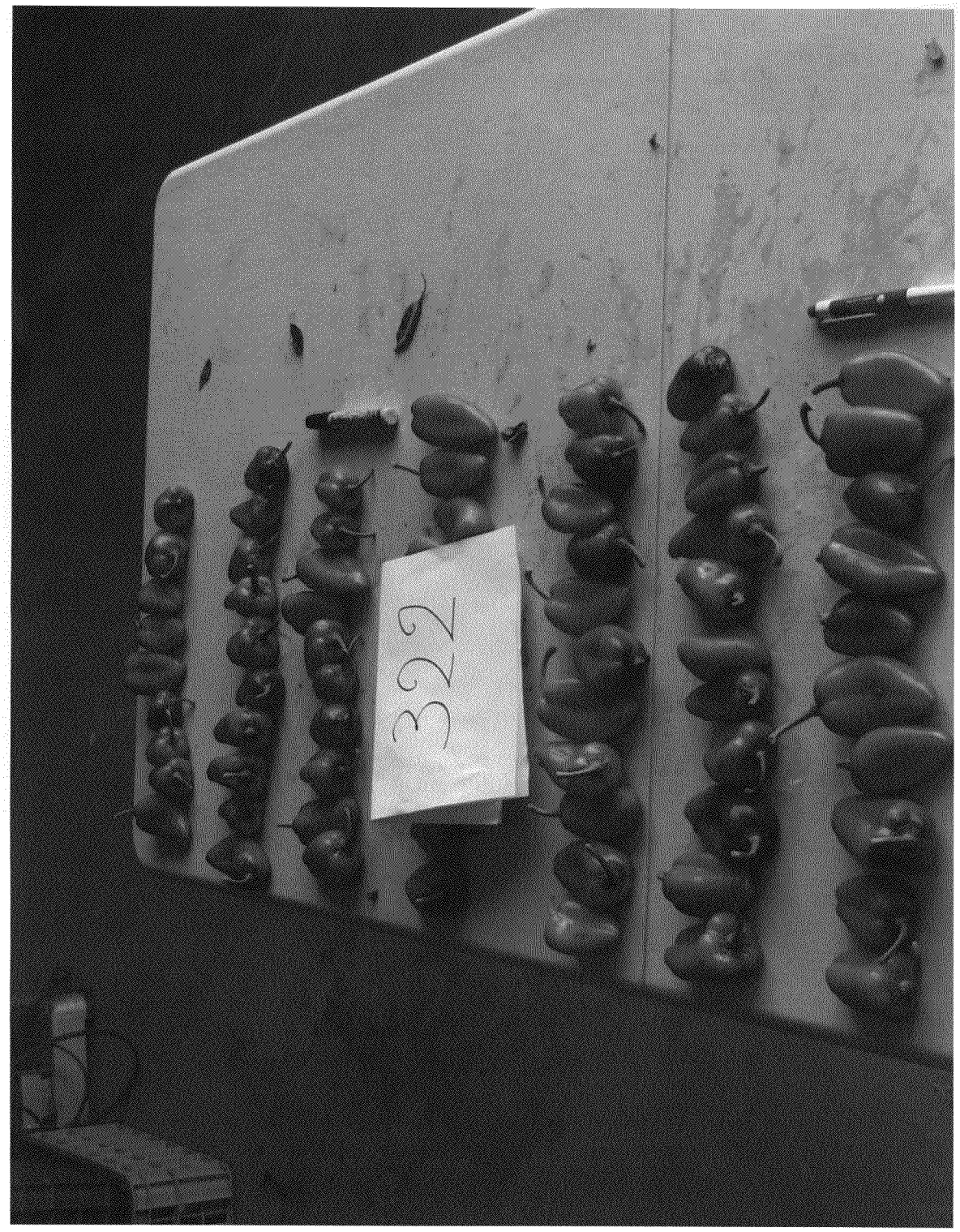
322